(12) United States Patent
Imperante

(10) Patent No.: US 6,245,924 B1
(45) Date of Patent: Jun. 12, 2001

(54) FLUORINATED DIMETHICONE COPOLYOL PHOSPHATE QUATERNARY COMPOUNDS

(75) Inventor: John Imperante, Califon, NJ (US)

(73) Assignee: Phoenix Research Corp., Somerville, NJ (US)

( * ) Notice: Subject to any disclaimer, the term of this patent is extended or adjusted under 35 U.S.C. 154(b) by 14 days.

(21) Appl. No.: 09/686,231

(22) Filed: Oct. 12, 2000

(51) Int. Cl.$^7$ ............................................. C07F 7/10
(52) U.S. Cl. ............................................. 556/405; 528/28
(58) Field of Search ............................... 556/405; 528/28

(56) References Cited

U.S. PATENT DOCUMENTS 6,087,517 * 7/2000 O'Lenick, Jr. ....................... 556/405
6,175,028 * 1/2001 O'Lenick, Jr. ....................... 556/405

* cited by examiner

*Primary Examiner*—Paul F. Shaver

(57) ABSTRACT

The invention relates to a series of novel quaternized silicone fluorinated dimethicone copolyol phosphates. This class of compounds are outstandingly mild detergents and emulsifiers that provide breathable barriers when applied to hair and skin. These emulsions allow for delivery of barriers to the skin that allow for the passage of water and air through the barrier, but do not allow for the passage of oils. The compounds of the present invention are prepared by reacting a the aqueous salt a fluoro dimethicone copolyol phosphate disclosed in U.S. Pat. No. 6,087,517 with a 3-chloro-2-hydoxypropyl-quaternary compound.

20 Claims, No Drawings

FLUORINATED DIMETHICONE COPOLYOL PHOSPHATE QUATERNARY COMPOUNDS

BACKGROUND OF THE INVENTION

1. Field of the Invention

The invention relates to a series of novel quaternized silicone fluorinated dimethicone copolyol phosphates. This class of compounds are outstandingly mild detergents and emulsifiers that provide breathable barriers when applied to hair and skin. These emulsions allow for delivery of barriers to the skin that allow for the passage of water and air through the barrier, but do not allow for the passage of oils. The compounds of the present invention are prepared by reacting a the aqueous salt a fluoro dimethicone copolyol phosphate disclosed in U.S. Pat. No. 6,087,517 with a 3-chloro-2-hydoxypropyl-quaternary compound.

I have unexpectedly found that the incorporation of the cationic group into the backbone of the silicone molecule results in a series of compounds that are very mild detergents and emulsifiers as well as very effective in the delivery of the barrier properties to the skin, when compared to traditional surfactants and silicone compounds. The inclusion of the cationic group on the compound containing fluoro groups and silicone groups has significantly improved substantivity to hair and skin. It also provides excellent antistatic properties. The presence of the silicone and phosphate provides mildness and improved combability on hair, both wet and dry. Consequently, the compounds of the present invention are truly multifunctional materials in personal care applications.

The compounds of the present invention are prepared by reacting the compounds of U.S. Pat. No. 6,087,517 issued July 2000, with a 3-chloro-2-hydoxypropyl-quaternary compound.

The compounds find application in a variety of applications, most importantly the skin care segment of the personal care market.

2. Arts and Practices

Silicone compounds have been known to be active at the surface of cellulosic and synthetic fibers as well as paper. They are good nondurable lubricants and are very stable to oxidation, however, their high cost and lack of efficiency at low concentrations as well as low durability have made their acceptance in commercial products quite low.

In addition to their high cost, silicone compounds have little or no solubility in mineral oils, fatty triglycerides and other classical fatty quaternary compounds used for softening. This has resulted in the inability to prepare stable blends for use as a textile fiber treatment.

U.S. Pat. No. 5,164,471 issued in October 1992 to O'Lenick teaches that fluoro polyesters of silanols can be prepared by the reaction of a silanol, fluorine containing alcohol and a diacid.

U.S. Pat. No. 5,446,114 to O'Lenick issued in August 1995, discloses the fluoro dimethicone copolyol compounds used as raw materials in the present invention. This invention failed to recognize the added benefits of the phosphate functionality when added to the molecule replacing the hydroxyl functionality.

U.S. Pat. No. 6,087,517 to O'Lenick discloses the fluoro dimethicone copolyol phosphate useful as a raw material in the practice of the current invention. The compounds disclosed in this patent are neutralized to a pH of 10–11 with suitable base and reacted with a 3-chloro-2-hydoxypropyl-quaternary compound, to make the compounds of the present invention.

None of these cited patents teach the incorporation of the fluoro group, the silicone group, phosphate group, an alkylene oxide group and a cationic quaternary group. All groups are vital to the functionality of the compounds of the present invention.

THE INVENTION

Object of the Invention

It is the object of the present invention to provide a series of novel fluorine containing dimethicone copolyol phosphates , onto which has been placed a fatty cationic group. Since the phosphate group will be anionic and the quat group cationic, the overall charge on the compound will be zero. The compound therefore is an amphoteric. These materials are very mild detergents and emulsifiers and possess unique barrier properties and are very substantive to the skin when applied in aqueous systems.

Summary of the Invention

The present invention relates to a series of novel amphoteric fluoro dimethicone copolyol polymers. The compounds of the present invention are prepared by reacting a series of fluoro dimethicone copolyol phosphates disclosed in U.S. Pat. No. 6,087,517, with a 3-chloro-2-hydoxypropyl-quaternary compound, to make the compounds of the present invention.

As will become clear from the disclosure, the compounds of the present invention having all groups discussed present in the molecule, result in multi-functional phospholipid like molecules group present, resulting in a mild detergent system that has a differentially permeable film and improved skin substantivity.

The compounds of the present invention conform to the following structure;

Terminal Compounds $$R'-\underset{\underset{Me}{|}}{\overset{\overset{Me}{|}}{Si}}-\left[O-\underset{\underset{R}{|}}{\overset{\overset{Me}{|}}{Si}}\right]_p-O-\underset{\underset{Me}{|}}{\overset{\overset{Me}{|}}{Si}}-R$$

wherein;

p is an integer ranging from 1 to 2,000;

Me is methyl;

R' is $$-(CH_2)_3-O-(EO)_{\overline{a}}-(PO)_{\overline{b}}-(EO)_{\overline{c}}-\underset{\underset{R^1-{}^+N(CH_3)_2-CH_2CH(OH)CH_2}{|}}{P(O)}-O^-$$

$R^1$ is $CH_3-(CH_2)e-$ ;

e is an integer ranging from 0 to 13;

R is $-(CH_2)_2-(CF_2)_s-CF_3$;

s is an integer ranging from 1 to 13;

a, b and c are each independently integers ranging from 0 to 20;

EO is $-(CH_2CH_2-O)-$;

PO is a —(CH$_2$CH$_2$—O)—.

Comp Compounds

Me—Si(Me)(Me)—[O—Si(Me)(R)]$_o$—[O—Si(Me)(Me)]$_q$—[O—Si(R')(Me)]$_t$—O—Si(Me)(Me)—Me wherein;

Me is methyl;

o is an integer ranging from 1 to 20;

t is an integer ranging from 1 to 20;

q is an integer ranging from 0 to 2000;

R' is

—(CH$_2$)$_3$—O—(EO)$_a$—(PO)$_b$—(EO)$_c$—P(O)—O$^-$
$\quad\quad\quad\quad\quad\quad\quad\quad\quad\quad$ |
$\quad\quad\quad\quad$ R$^1$—$^+$N(CH$_3$)$_2$—CH$_2$CH(OH)CH$_2$ R$^1$ is CH$_3$—(CH$_2$)$_e$- e is an integer ranging from 0 to 21;

R is —(CH$_2$)$_2$—(CF$_2$)$_s$—CF$_3$;

s is an integer ranging from 1 to 13;

a, b and c are each independently integers ranging from 0 to 20;

EO is —(CH$_2$CH$_2$—O)—;

PO is a —(CH$_2$CH(CH$_3$)—O)—.

Preferred Embodiments

In a preferred embodiment the compounds are comb compounds.

In a preferred embodiment the compounds are terminal compounds.

In a preferred embodiment s is 1.

In a preferred embodiment s is 5.

In a preferred embodiment s is 7.

In a preferred embodiment s is 10.

In a preferred embodiment s is 13.

In a preferred embodiment e is 0.

In a preferred embodiment e is 11.

In a preferred embodiment e is 15.

In a preferred embodiment e is 17.

In a preferred embodiment e is 21.

The preferred concentration of product in water ranges from 20–50% by weight. The more preferred ranges from 30–40% by weight and the most preferred is 35% solids by weight.

EXAMPLES

Intermediates

The following examples are taken from U.S. Pat. No. 5,446,114 to O'Lenick, Jr., incorporated herein by reference. They are intermediates for the preparation of the compounds of the present invention.

| Example | U.S. Pat. No. 5,446,114 Example Number |
|---|---|
| 1 | 22 |
| 2 | 23 |
| 3 | 24 |
| 4 | 25 |
| 5 | 26 |
| 6 | 27 |
| 7 | 28 |
| 8 | 29 |
| 9 | 30 |
| 10 | 31 |
| 11 | 32 |
| 12 | 33 |
| 13 | 34 |

Preparation of Fluoro dimethicone copolyol phosphate

Phosphating Agents

Polyphosphoric Acid (PPA) is 115% phosphoric acid. When used as a phosphating agent in gives more mono ester than the phosphorus pentoxide.

Phosphorus pentoxide is P$_2$O$_5$. It is more aggressive in phosphation and results in more diester.

The silicone phosphates of this invention can be prepared by reacting the hydroxyl containing silicone polymer with a suitable phosphating agent. Preferred phosphating reagents are polyphosphoric acid and phosphorus pentoxide.

The preparation of the novel silicone phosphates of this invention from the hydroxy silicone compounds can be illustrated by the following reaction in which R is the hydroxy silicone compound.

Phosphation Reaction Sequence

R—OH + P205 ⟶

(R—O)—P(O)—(OH)2 and (R—O—)2P(O)—(OH)

$\quad\quad\quad\quad\quad\quad\quad\quad\quad\quad$ ↓ Neutralization KOH/Water (R—O)—P(O)—(OK)2 and (R—O—)2P(O)—(OK)

It will be understood by the above reaction that the product of phosphation, weather using polyphosphoric acid or phosphorus pentoxide give a mixture of mono and di ester.

The following examples further illustrate the objects and advantages of this invention, though it should be understood that the various reactants and amounts thereof, reaction conditions, and other details are merely illustrative and should not be construed to unduly limit this invention.

General Procedure

The specified amount of fluoro hydroxy silicone compound (Examples 1–13) is added to a suitable reaction vessel. The specified amount of either polyphosphoric acid or phosphorus pentoxide is charged to under good agitation over a 2 hr. period. The exothermic reaction raises the temperature of the mixture to about 70 C. After 1 hour slowly raise the temperature to 100 C. and hold 2–4 hours.

| | Fluoro DMC | | Polyphosphoric Acid |
|---|---|---|---|
| Example | Example | Grams | Grams |
| 14 | 1 | 3673.0 | 56.5 |
| 15 | 2 | 15161.0 | 56.6 |
| 16 | 3 | 149190.0 | 56.6 |
| 17 | 4 | 38408.0 | 56.6 |
| 18 | 5 | 964.0 | 56.6 |
| 19 | 6 | 1107.0 | 56.6 |
| 20 | 7 | 902.0 | 56.6 |
| 21 | 8 | 11056.0 | 56.6 |
| 22 | 9 | 148900.0 | 56.6 |
| 23 | 10 | 40240.0 | 56.6 |
| 24 | 11 | 5269.0 | 56.6 |
| 25 | 12 | 1264.0 | 56.6 |
| 26 | 13 | 1492.0 | 56.6 |
| | | Phosphorus Pentoxide | |
| 27 | 1 | 3673.0 | 36.0 |
| 28 | 2 | 15161.0 | 36.0 |
| 29 | 3 | 149190.0 | 36.0 |
| 30 | 4 | 38408.0 | 36.0 |
| 31 | 5 | 964.0 | 36.0 |
| 32 | 6 | 1107.0 | 36.0 |
| 33 | 7 | 902.0 | 36.0 |
| 34 | 8 | 11056.0 | 36.0 |
| 35 | 11 | 5269.0 | 36.0 |
| 36 | 12 | 1264.0 | 36.0 |
| 37 | 13 | 1492.0 | 36.0 |

The compounds of the present invention are made by reacting the aqueous salt of the above compounds (examples 14–37) with 3-chloro-2 hydroxypropyl alkyl dimethyl ammonium chloride.

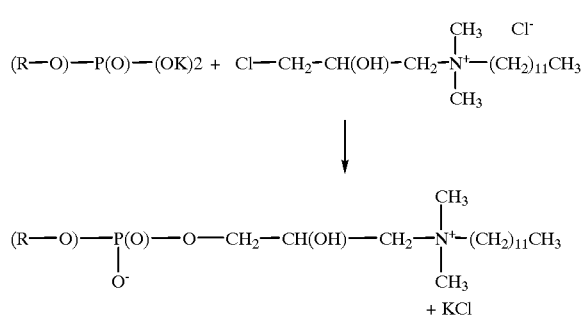

Examples 3-chloro-2-hydroxypropyl-alkyl-dimethyl-ammonium chloride Compounds of this type are commercially available from DeGussa and are sold under the tradename "Quab". They are also available from Dow Chemical.

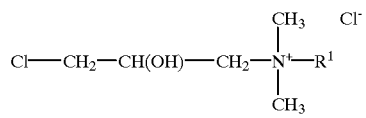

wherein;

$R^1$ is $CH_3-(CH_2)_e-$ e is integer ranging from 0 to 21;

| Example | "e" Value |
|---|---|
| 38 | 0 |
| 39 | 7 |
| 40 | 11 |
| 41 | 15 |
| 42 | 17 |
| 43 | 21 |

General Procedure

In a suitable vessel the is added the specified number of grams of fluoro silicone phosphate (Example 14–37). The specified number of grams of water it then added. The pH is adjusted to 10.5, using either KOH, NaOH. Next the specified amount of chloro compound is added (Examples 38–43). The reaction mass is heated to 90–95° C. and held for 4–6 hours. The reaction progress is followed by the generation of inorganic chloride ion. Once it reaches 97% of theoretical the reaction is considered complete. The product is used without additional purification.

| | Fluoro Silicone Phosphate | | Chloro Compound | | Base | Water |
|---|---|---|---|---|---|---|
| Example | Example | Grams | Example | Grams | Type | Grams |
| 44 | 14 | 372.9 | 38 | 15.3 | KOH | 698 |
| 45 | 15 | 1521.7 | 39 | 25.1 | KOH | 2785 |
| 46 | 16 | 14924.7 | 40 | 30.7 | KOH | 26919 |
| 47 | 17 | 3846.4 | 41 | 36.3 | KOH | 7000 |
| 48 | 18 | 102.0 | 42 | 39.1 | KOH | 254 |
| 49 | 19 | 116.4 | 43 | 44.7 | KOH | 290 |
| 50 | 20 | 96.0 | 38 | 15.3 | KOH | 200 |
| 51 | 21 | 1111.2 | 39 | 25.1 | KOH | 2045 |
| 52 | 22 | 14895.7 | 40 | 30.7 | KOH | 26867 |
| 53 | 23 | 4029.6 | 41 | 36.3 | KOH | 7318 |
| 54 | 24 | 532.6 | 42 | 39.1 | KOH | 1029 |
| 55 | 25 | 132.1 | 43 | 44.7 | KOH | 318 |
| 56 | 26 | 20.6 | 38 | 15.3 | KOH | 65 |
| 57 | 27 | 307.9 | 39 | 25.1 | NaOH | 599 |
| 58 | 28 | 155.2 | 40 | 30.7 | NaOH | 335 |
| 59 | 29 | 14923.0 | 41 | 36.3 | NaOH | 26927 |
| 60 | 30 | 3844.4 | 42 | 39.1 | NaOH | 6968 |
| 61 | 31 | 100.0 | 43 | 44.7 | NaOH | 260 |
| 62 | 32 | 114.3 | 43 | 44.7 | NaOH | 286 |
| 63 | 33 | 93.8 | 42 | 39.1 | NaOH | 239 |
| 64 | 34 | 1109.2 | 41 | 36.3 | NaOH | 2062 |
| 65 | 35 | 530.5 | 40 | 30.7 | NaOH | 1010 |
| 66 | 36 | 130.0 | 39 | 25.1 | NaOH | 280 |
| 67 | 37 | 152.8 | 38 | 15.3 | NaOH | 302 |

The compounds of the present invention are used as prepared and are outstanding additives to personal care products like shampoos and bath products. They have a unique combination of forming thin films, are mild detergents and emulsifiers, and provide outstanding conditioning and softening on hair and skin.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains

What is claimed:

1. A polymer which conforms to the following structure:

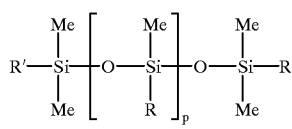

wherein;

is an integer ranging from 1 to 2,000;
Me is methyl;
R' is

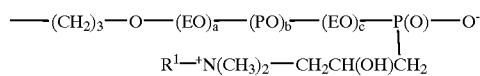

$R^1$ is $CH_3-(CH_2)_e-$
e is an integer ranging from 0 to 21;
R is $-(CH_2)_2-(CF_2)_s-CF_3$;
s is an integer ranging from 1 to 13;
a, b and c are each independently integers ranging from
EO is $-(CH_2H_2-O)-$;
PO is a $-(CH_2CH(CH_3)-O)-$.

2. A polymer of claim 1 wherein s is 1.
3. A polymer of claim 1 wherein s is 5.
4. A polymer of claim 1 wherein s is 7.
5. A polymer of claim 1 wherein s is 10.
6. A polymer of claim 1 wherein s is 13.
7. A polymer of claim 1 wherein e is 0.
8. A polymer of claim 1 wherein e is 11.
9. A polymer of claim 1 wherein e is 17.

10. A polymer which conforms to the following structure

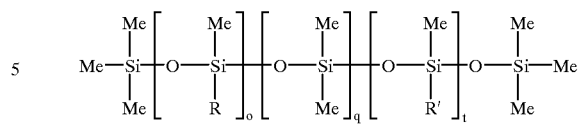

wherein;

Me is methyl;
o is an integer ranging from 1 to 20;
t is an integer ranging from 1 to 20;
q is an integer ranging from 0 to 2000;
R' is

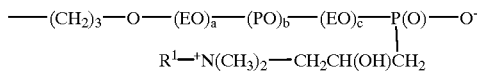

$R^1$ is $CH_3-(CH_2)_e-$
e is an integer ranging from 0 to 21;
R is $-(CH_2)_2-(CF_2)_s-CF_3$;
s is an integer ranging from 1 to 13;
a, b and c are each independently integers ranging from 0 to 20;
EO is $-(CH_2CH_2-O)-$;
PO is a $-(CH_2CH(CH_3)-O)-$.

11. A polymer of claim 10 wherein s is 1.
12. A polymer of claim 10 wherein s is 5.
13. A polymer of claim 10 wherein s is 7.
14. A polymer of claim 10 wherein s is 10.
15. A polymer of claim 10 wherein s is 13.
16. A polymer of claim 10 wherein e is 0.
17. A polymer of claim 10 wherein e is 11.
18. A polymer of claim 10 wherein e is 17.
19. A polymer of claim 10 wherein e is 15.
20. A polymer of claim 10 wherein e is 21.

* * * * *